United States Patent [19]

Edwards

[11] 4,144,335
[45] Mar. 13, 1979

[54] INSECTICIDAL 2-SUBSTITUTED-IMINO-3-ALKYL-5-DIALK-OXYPHOSPHINOTHIOYLOXY-6H-1,3,4-THIADIAZINE

[75] Inventor: Laroy H. Edwards, Napa, Calif.

[73] Assignee: Chevron Research Company, San Francisco, Calif.

[21] Appl. No.: 889,757

[22] Filed: Mar. 24, 1978

[51] Int. Cl.$^2$ .................... C07D 285/16; A01N 9/36
[52] U.S. Cl. ........................................ 424/246; 544/8
[58] Field of Search ...................... 424/246; 544/8

[56] References Cited

U.S. PATENT DOCUMENTS 3,514,455   5/1970   Takamizawa et al. ................. 544/8

FOREIGN PATENT DOCUMENTS 44-28102   11/1969   Japan .......................... 544/8

OTHER PUBLICATIONS

Ruefenacht, Chem. Abstr., vol. 80, entry 82906 (1974)
Helv. Chim Acta, vol. 56, pp. 2186–2204 (1973).

Primary Examiner—John M. Ford
Attorney, Agent, or Firm—Dix A. Newell; T. G. DeJonghe

[57] ABSTRACT

Thiadiazine compounds of the formula (I)

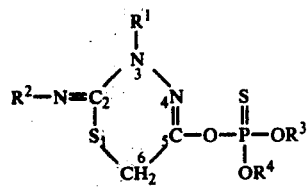

wherein $R^1$ is alkyl, $R^2$ is alkyl, cycloalkyl, alkenyl or aryl, $R^3$ is alkyl and $R^4$ is alkyl, are useful as insecticides. The thiadiazine compounds are prepared by the addition of a dialkylhalothiophosphate to a tetrahydro-6H-1,3,4-thiadiazin-5-one.

12 Claims, No Drawings

INSECTICIDAL 2-SUBSTITUTED-IMINO-3-ALKYL-5-DIALKOXY-PHOSPHINOTHIOYLOXY-6H-1,3,4-THIADIAZINE

DESCRIPTION OF THE PRIOR ART

Chemical Abstract, Vol. 80, 82906 p (1974) discloses thiadiazinones and their mono- and dithiophosphates.

DESCRIPTION OF THE INVENTION

The insecticidal compounds of the invention are represented by the formula

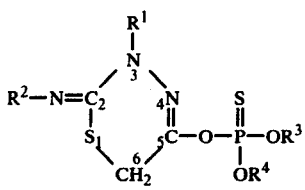

wherein $R^1$ is alkyl of 1 to 6 carbon atoms, $R^2$ is alkyl of 1 to 6 carbon atoms, alkenyl of 3 to 6 carbon atoms, cycloalkyl of 5 to 6 carbon atoms, phenyl, or phenyl substituted with 1 to 2 substituents selected from the group consisting of alkyl of 1 to 6 carbon atoms, fluoro, chloro, bromo, iodo, nitro, trifluoromethyl, trichloromethyl, tribromomethyl and alkoxy of 1 to 4 carbon atoms, $R^3$ is alkyl of 1 to 6 carbon atoms and $R^4$ is alkyl of 1 to 6 carbon atoms.

Representative alkyl $R^1$, $R^2$, $R^3$, and $R^4$ groups include methyl, ethyl, isopropyl, n-butyl, isohexyl, n-hexyl, etc.

Representative substituted phenyl $R^2$ groups include 4-methylphenyl, 2,4-dimethylphenyl, 2-fluorophenyl, 3,5-dichlorophenyl, 3-bromophenyl, 4-iodophenyl, 2-methyl-4-chlorophenyl, 4-nitrophenyl 3-trichloromethylphenyl, 2-methoxyphenyl and 2-chloro-4-nitrophenyl. Representative alkenyl $R^2$ groups are allyl, 2-butenyl and 3-hexenyl.

Preferably $R^1$ is lower alkyl of 1 to 3 carbon atoms, especially methyl.

Preferred alkyl $R^2$ groups are alkyl of 1 to 4 carbon atoms and preferred aryl $R^2$ groups are phenyl and phenyl substituted with 1 to 2 substituents selected from alkyl of 1 to 4 carbon atoms, fluoro, chloro, bromo, trifluoromethyl and trichloromethyl. Preferably, $R^2$ is alkyl of 1 to 4 carbon atoms.

Preferably $R^2$ and $R^3$ are alkyl of 2 to 4 carbon atoms, especially ethyl.

A preferred class of thiadiazines of formula I is that wherein $R^1$ is lower alkyl of 1 to 3 carbon atoms, especially methyl, $R^2$ is alkyl of 1 to 6 carbon atoms, $R^3$ is alkyl of 2 to 4 carbon atoms and $R^4$ is alkyl of 2 to 4 carbons.

The compounds of the invention are prepared by the addition of a dialkoxyhalothiophosphate (III) to a 2-(substitutedimino)-3-alkyl-tetrahydro-6H-1,3,4-thiadiazin-5-one (II), as depicted in the following reaction (1)

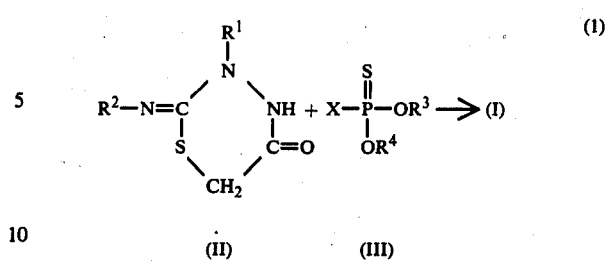

wherein $R^1$, $R^2$, $R^3$ and $R^4$ have the same meaning as stated before, and X is chloro or bromo, preferably chloro.

Reaction (1) is generally conducted by reacting substantially equimolar amounts of the thiadiazinone (II) and the thiophosphate (III), i.e., the molar ratios of thiadiazinone (II) to thiophosphate (III) generally vary from about 1:1.2 to 1.2:1, although molar ratios from about 1:1.1 to 1.1:1 are preferred. A substantially equivalent amount of a base material is used to scavenge the hydrogen halide by-product. Such bases are preferably inorganic bases, e.g., alkali metal carbonates such as sodium carbonate and potassium carbonate, and alkali metal bicarbonates such as sodium bicarbonate. The molar ratio of base to the thiadiazinone (II) is generally about 1.1:1 to 1:1. The reaction is conducted in an inert liquid organic diluent. Suitable inert organic diluents include alkanones such as acetone, methyl ethyl ketone; acyclic alkyl ethers such as dimethoxyethane and dibutylether; cyclic ethers such as dioxane or tetrahydrofuran; haloalkanes such as dichloromethane and aromatic compounds such as benzene, toluene, and chlorobenzene. Generally, the amount of diluent employed ranges from 1 to 50 mols per mol thiophosphate (II).

Reaction (1) is suitably conducted at a temperature of from about 15° C. to the boiling point of the diluent, although temperatures of from about 20° C. to 100° C. are preferred. The reaction is conducted at or above atmospheric pressure. The reaction time will, of course vary depending on the reaction temperature and the particular reactants employed. Generally, however, the reaction time varies from several minutes to 24 hours. The thiadiazine product (I) is isolated from the reaction mixture by conventional procedures, e.g., extraction, chromatography, crystallization, etc.

Reaction (1) may also be conducted with the hydrogen halide salts of the thiadiazinone (II). In this modification of reaction (1), two equivalents of the base material is used, i.e, the molar ratio of base to thiadiazinone is generally about 2.2:1 to 2:1. It is generally preferred to use the hydrogen halide salt when the imino substituent ($R^2$) of the thiadiazinone (II) is aliphatic.

The thiadiazin-5-one reactants (II) used in reaction (1) are novel compounds and are prepared by the cyclization of a semithiocarbazide (IV) with a haloacetic anhydride (V), as depicted in the following reaction (2):

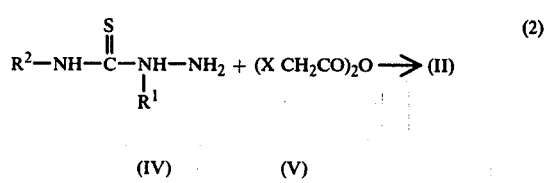

wherein $R^1$, $R^2$ and X have the same meaning as previously stated.

Reaction (2) is generally conducted by reaction substantially equimolar amounts of the semithiocarbazide (IV) and the haloacetic anhydride (V) in the liquid phase. The molar ratios of semithiocarbazide to anhydride (V) generally vary from about 1:1.2 to 1.2:1, although molar ratios of from about 1:1.1 to 1.1:1 are preferred. The reaction is normally conducted in an inert liquid diluent, e.g., organic solvents such as chlorinated hydrocarbons. The reaction is conducted at a temperature of from about 0° to the boiling point of the diluent, although temperatures from about 25° C. to 100° C. are preferred. The reaction is conducted at or above atmospheric pressure. Generally, the reaction is completed within one-half to 24 hours. The product (II) is isolated and purified by conventional procedures such as extraction, filtration, crystallization and chromatography. Generally, when the thiadiazinone product (II) has an aliphatic imino substituent ($R^2$), the product is most conveniently isolated as a hydrogen halide salt.

The thiadiazin-5-one reactants (II) are also be prepared by reacting the semithiocarbazide (IV) with an alkyl halothioacetate (VI) as depicted in the following reaction (3):

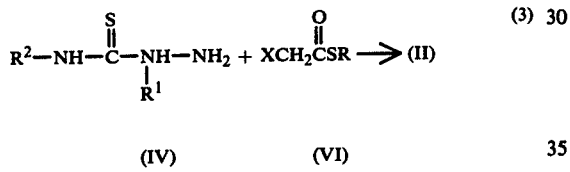

(IV)    (VI)      (3)

wherein $R^1$, $R^2$ and X have the same meaning as previously stated and R is alkyl of 1 to 6 carbon atoms, preferably of 1 to 3 carbon atoms.

Reaction (3) is generally conducted by reacting substantially equimolar amounts of the semithiocarbazide (IV) and the halothioacetate (VI) in the liquid phase. The molar ratios of semithiocarbazide to halothioacetate (VI) generally vary from about 1:1.2 to 1.2:1, although molar ratios of from about 1:1.1 to 1.1:1 are preferred. The reaction is normally conducted in an inert liquid diluent. Suitable inert organic diluents include alkanones such as acetone, methyl ethyl ketone; acyclic alkyl ethers such as dimethoxyethane and dibutylether; cyclic ethers such as dioxane or tetrahydrofuran; haloalkanes such as dichloromethane; and aromatic compounds such as benzene, toluene, and chlorobenzene. Generally, the amount of diluent employed ranges from 1 to 50 mols per mol of semithiocarbazide (IV). The reaction is conducted at a temperature of from about 0° C. to the boiling point of the diluent, although temperatures from about 25° C. to 100° C. are preferred. The reaction is conducted at or above atmospheric pressure. Generally, the reaction is completed within one-half to 24 hours. The product (II) is isolated and purified by conventional procedures such as extraction, filtration, crystallization chromatography. Generally, when the thiadiazinone product (II) has an aliphatic imino substituent ($R^2$), the product is most conveniently isolated as a hydrogen halide salt.

EXAMPLE 1

Preparation of 2-(3,4-dichlorophenylimino)-3-methyl-tetrahydro-6H-1,3,4-thiadiazin-5-one To a stirred solution of 37.5 g (0.15 mol) 2-methyl-4-(3,4-dichlorophenyl)semithiocarbazide in 200 ml dichloromethane was added 25.5 g (0.015 mol) chloroacetic anhydride. The resulting reaction mixture was heated under reflux for 16 hours, cooled, neutralized with sodium bicarbonate, washed with water, dried over magnesium sulfate and evaporated under reduced pressure to give an oily solid. The solid was slurried with ether, filtered and dried to give 12 g of the product, as a grey solid, m.p. 118°–120° C. This product is tabulated in Table A as compound No. A-6.

EXAMPLE 2

Preparation of 2-(3,4-dichlorophenylimino)-3-methyl-5-diethoxyphosphinothioyloxy)-2,3-dihydro-6H-1,3,4-thiadiazine A slurry of 14 g (0.048 mol) 2-(3,4-dichlorophenylimino)-3-methyl-tetrahydro-6H-1,3,4-thiadizin-5-one, 7 g (0.048 mol) potassium bicarbonate, and 9.1 g (0.048 mol) diethylchlorothiophosphate in 200 ml acetone was heated under reflux for 8 hours, cooled and stirred at about 25° C. for overnight. The reaction mixture was filtered and evaporated under reduced pressure to give an oil. The oil was chromatographed on silica gel using 50/50 petroleum ethyl/diethyl ether as the eluant to give 11 g of the product, as a yellow oil. This product is tabulated in Table B, as compound B-7.

EXAMPLE 3

Preparation of 2-(t-butylimino)-3-methyl-tetrahydro-6H-1,3,4-thiadiazin-5-one hydrochloride To a stirred solution of 16.1 g (0.1 mol) 2-methyl-4-t-butylsemithiocarbazide in 200 ml dichloromethane was added slowly 17.1 g (0.1 mol) chloroacetic anhydride. The resulting solution was stirred at about 25° C. for about 8 hours. The reaction mixture was filtered to give 14 g of the product, as a white solid, m.p., 224°–225° C. The infrared spectrum of the product showed carbonyl absorption at 5.95 micron. Elemental analysis for $C_8H_{16}ClN_3OS$ showed:

|  | Calc. | Found |
|---|---|---|
| %S | 13.5 | 13.3 |
| %Cl | 14.9 | 15.5 |

EXAMPLE 4

Preparation of 2-(t-butylimino)-3-methyl-5-diethoxyphosphinothioyloxy-2,3-dihydro-6H-1,3,4,-thiadiazine A slurry of 10.0 g (0.0421 mol) 2-(t-butylimino)-3-methyl-6H-1,3,4-thiadiazin-5-one, 11.6 g (0.0842 mol) potassium carbonate and 8.2 g (0.0421) diethylchlorothiophosphate in 200 ml acetone was heated under reflux for 8 hours. The reaction mixture cooled, stirred overnight, filtered and evaporated under reduced pressure to give an oil residue. The residue was dissolved in dichloromethane, washed with water, dried over magnesium sulfate and evaporated under reduced pressure.

The crude product was then chromatographed on silica gel using diethyl ether as the eluant. The purified product (6 g) was an amber oil. The product is tabulated in Table B as Compound No. B-1.

EXAMPLE 5

Preparation of 2-(t-butylimino)-3-methyl-6H-1,3,4-thiadiazin-5-one hydrobromide

To a stirred solution of 5.75 g (0.05 mol) 2-methyl-4-t-butylsemithiocarbazide in 50 ml dichloromethane was added dropwise 9.15 g (0.05 mol) ethyl alpha-bromothioacetate at 25° C. The reaction mixture was stirred at 25° C. for 20 minutes (slightly exothermic reaction) and then heated under reflux for 4 hours. After cooling, the precipitated solid was filtered, washed with hexane and dried to give 7.3 g of product, m.p. 215°–216° C.

The compounds tabulated in Tables A and B were prepared by procedures similar to those of Examples 1–5. The structure of each compound tabulated in Tables A and B was confirmed by nuclear magnetic resonance and/or infrared spectroscopy.

UTILITY

The thiadiazine compounds of this invention were tested as follows to illustrate their insecticidal activity. Test results are reported in Table C.

Test Procedures

Aphid (*Aphis gossypii* Glover): An acetone solution of the candidate toxicant containing a small amount of nonionic emulsifier was diluted with water to 40 ppm. Cucumber leaves infested with the cotton aphids were dipped in the toxicant solution. Mortality readings were then taken after 24 hours.

Two-spotted Mite (*Tetramuchus urticae*): An acetone solution of the candidate toxicant containing a small amount of nonionic emulsifier was diluted with water to 40 ppm. Lima bean leaves which were infested with mites were dipped in the toxicant solution. Mortality readings were taken after 24 hours.

Housefly (*Musca domestica* L.): A 500 ppm acetone solution of the candidate toxicant was placed in a microsprayer (atomizer). A random mixture of anesthetized male and female flies was placed in a container and

TABLE A

Compounds of the formula $$R^2-N=C \begin{array}{c} CH_3 \\ | \\ N \\ \diagup \quad \diagdown \\ \quad \quad NH \\ | \quad\quad | \\ S \quad\quad C=O \\ \diagdown \quad \diagup \\ CH_2 \end{array}$$

| No. | $R^2$ | m.p., °C. | C Calc. | C Found | H Calc. | H Found | N Calc. | N Found |
|---|---|---|---|---|---|---|---|---|
| A-1 | 4-Cl-φ | 143–145 | — | — | — | — | 12.5[1] | 13.2[1] |
| A-2 | i-C$_3$H$_7$ | 122–124 | — | — | — | — | 14.1[1] | 13.8[1] |
| A-3 | n-C$_3$H$_7$ | 126–130 | 37.6 | 35.6 | 6.3 | 5.9 | 18.2 | 17.2 |
| A-4 | t-C$_4$H$_9$ | 127–129 | 40.4 | 39.3 | 6.8 | 6.6 | 17.7 | 17.1 |
| A-5 | 3-CF$_3$-φ | 83–84 | 45.7 | 44.4 | 3.5 | 4.1 | 14.5 | 15.0 |
| A-6 | 3,4-Cl$_2$-φ | 118–120 | 41.4 | 40.7 | 3.1 | 3.1 | 14.5 | 14.1 |
| A-7 | φ | 140–144 | 46.6 | 43.4 | 4.7 | 4.8 | 16.3 | 15.5 |
| A-8 | cyclohexyl | 133–135 | 45.6 | 47.1 | 6.9 | 7.8 | 15.9 | 16.8 |
| A-9 | CH$_2$=CHCH$_2$ | 68–70 | 37.9 | 35.1 | 5.5 | 5.6 | 19.0 | 17.9 |
| A-10 | φ | 143–145 | 54.3 | 55.1 | 5.0 | 5.2 | 19.0 | 19.4 |

[1]Sulfur analysis
φ represents phenyl.

TABLE B

Compounds of the formula $$R^2-N=C \begin{array}{c} CH_3 \\ | \\ N \\ \diagup \quad \diagdown \\ \quad\quad N \quad\quad S \\ | \quad\quad \| \quad\quad \| \\ S \quad C-O-P-OR^3 \\ \diagdown \quad \diagup \quad\quad | \\ CH_2 \quad\quad OR^4 \end{array}$$

| No. | $R^2$ | $R^3$ | $R^4$ | m.p., °C. | C Calc. | C Found | H Calc. | H Found | N Calc. | N Found |
|---|---|---|---|---|---|---|---|---|---|---|
| B-1 | t-C$_4$H$_9$ | C$_2$H$_5$ | C$_2$H$_5$ | Oil | — | — | — | — | 18.1[1] | 17.9[1] |
| B-2 | n-C$_3$H$_7$ | C$_2$H$_5$ | C$_2$H$_5$ | Oil | — | — | — | — | 18.9[1] | 19.4[1] |
| B-3 | CH$_3$ | C$_2$H$_5$ | C$_2$H$_5$ | Oil | — | — | — | — | 20.6[1] | 20.6[1] |
| B-4 | cyclohexyl | C$_2$H$_5$ | C$_2$H$_5$ | Oil | 44.3 | 43.6 | 6.9 | 6.9 | 11.1 | 10.8 |
| B-5 | 2-F-φ | C$_2$H$_5$ | C$_2$H$_5$ | oil | 43.0 | 40.9 | 4.9 | 4.8 | 10.7 | 10.6 |
| B-6 | i-C$_3$H$_7$ | C$_2$H$_5$ | C$_2$H$_5$ | oil | 39.9 | 38.4 | 6.5 | 6.4 | 12.4 | 11.4 |
| B-7 | 3,4-Cl$_2$-φ | C$_2$H$_5$ | C$_2$H$_5$ | oil | 38.0 | 37.4 | 4.1 | 4.3 | 9.5 | 9.7 |
| B-8 | CH$_3$ | CH$_3$ | CH$_3$ | oil | 29.7 | 30.2 | 5.0 | 5.0 | 14.8 | 14.6 |
| B-9 | CH$_2$=CHCH$_2$ | C$_2$H$_5$ | C$_2$H$_5$ | oil | 39.2 | 37.1 | 6.0 | 5.7 | 12.5 | 11.5 |
| B-10 | φ | C$_2$H$_5$ | C$_2$H$_5$ | oil | 45.0 | 41.4 | 5.4 | 5.4 | 11.3 | 10.0 |
| B-11 | CH$_2$=CHCH$_2$ | CH$_3$ | CH$_3$ | oil | 35.0 | 36.7 | 5.2 | 5.2 | 13.6 | 13.7 |
| B-12 | i-C$_3$H$_7$ | CH$_3$ | CH$_3$ | oil | 34.7 | 36.1 | 5.8 | 6.0 | 13.5 | 13.5 |

[1]Sulfur analysis
φ represents phenyl.

55 mg of the above-described acetone solution was sprayed on them. A lid was placed on the container. A mortality reading was made after 24 hours.

American Cockroach (*Periplaneta americana* L.): A 500 ppm acetone solution of the candidate toxicant was placed in a microsprayer (atomizer). A random mixture of anesthetized male and female roaches was placed in a container and 55 mg of the above-described acetone solution was sprayed on them. A lid was placed on the container. A mortality reading was made after 24 hours.

Alfalfa Weevil (*H. brunneipennis Boheman*) A 500 ppm acetone solution of the candidate toxicant was placed in a microsprayer (atomizer). A random mixture of anesthetized male and female flies was placed in a container and 55 mg of the above-described acetone solution was sprayed on them. A lid was placed on the container. A mortality reading was made after 24 hours.

Rootworm (*Diabrotica u. undecimpunctate Mannerheim*): A batch of 20–30 two-day-old Diabrotica eggs was placed on the bottom edge of a 236-ml plastic cup. The cup then received the following materials:
(1) 66 g soil treated with 15 ppm of the test compound; (2) 15 ml water; (3) 10 presoaked (in water for 2 hours) corn seeds evenly distributed on the soil surface; (4) 66 g soil treated with 15 ppm of test compounds; and (5) 15 ml water. The cup was placed in an incubation chamber and lightly watered as needed to keep the soil damp. After 14–16 days the test cup was examined under a dissecting microscope by observing the core roots and soil through the clear plastic walls of the cup. Control of newly hatched larvae was rated by visually evaluating the degree of corn root damage by feeding larvae in conjunction with visible presence of live and/or dead larvae.

TABLE C

| | Insect Control, % | | | | | | |
| --- | --- | --- | --- | --- | --- | --- | --- |
| No. | Aphid | Mite | Housefly | Roach | Weevil | Rootworm | Looper |
| B-1 | 70 | 0 | 60 | 100 | 100 | 75 | 100 |
| B-2 | 100 | 99 | 90 | 0 | 100 | 80 | 20 |
| B-3 | 100 | 99 | 100 | 100 | 100 | 0 | 100 |
| B-4 | 85 | 0 | 0 | 0 | 0 | 0 | 0 |
| B-5 | 94 | 0 | 0 | 0 | 0 | 0 | 0 |
| B-6 | 99 | 94 | 100 | — | 100 | 78 | 50 |
| B-7 | 0 | 70 | 22 | — | 0 | 98 | 100 |
| B-8 | 99 | 98 | 99 | — | 100 | 0 | 80 |
| B-9 | 100 | 50 | 22 | 0 | 100 | 100 | 80 |
| B-10 | 98 | 0 | 0 | 0 | 0 | 100 | 80 |

The compounds of this invention are toxic to a variety of crop and household pests, in addition to the typical pests exemplified above. Like most agricultural chemicals, they are not usually applied full strength, but are generally incorporated with conventional biologically inert extenders or carriers normally employed for facilitating dispersion of active ingredients for agricultural chemical applications, recognizing the accepted fact that the formulation and mode of application may affect the activity of a material. The toxicants of this invention may be applied as sprays, dusts, or granules to the insects, their environment or hosts susceptible to insect attack. They may be formulated as granules of large particle size, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from 5–80% toxicant and the rest inert material which includes dispersing agents, emulsifying agents, and wetting agents. The powder may be applied to the soil as a dry dust or preferably as a suspension in water. Typical carriers include fuller's earth, kaolin clays, silicas, and other highly absorbent, readily wet, inorganic diluents. Typical wetting, dispersing, or emulsifying agents used in agricultural formulations include, for example, the alkyl and alkylaryl sulfonates and sulfonates and their sodium salts; alkylamide sulfonates, including fatty methyl taurides; alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long chain mercaptans and ethylene oxide. Many other types of useful surface-active agents are available in commerce. The surface-active agent, when used, normally comprises from 1% to 15% by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about fifty microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the toxicant with a liquid or solid emulsifying agent, or may also contain a liquid carrier, such as xylene, heavy aromatic naphthas, isophorone, and other non-volatile organic solvents. For application, these concentrates are dispersed in water or other liquid carrier, and normally applied as a spray to the area to be treated.

Other useful formulations for insecticidal applications include simple solutions of the active ingredient in a dispersant in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Baits, prepared by mixing solid or liquid concentrates of the toxicant with a suitable food, such as a mixture of cornmeal and sugar, are useful formulations for control of insect pests. Pressurized sprays, typically aerosols wherein the active ingredient is dispersed in finely divided form as a result of vaporization of a low-boiling dispersant solvent carrier, such as the Freons, may also be used. All of these techniques for formulating and applying the active ingredient are well known in the art.

The percentages by weight of the toxicant may vary according to the manner in which the composition is to be applied and the particular type of formulation, but in general comprises 0.1 to 95% of the toxicant by weight of the pesticidal composition.

The pesticidal compositions may be formulated and applied with other active ingredients, including other nematocides, insecticides, fungicides, bactericides, plant growth regulators, fertilizers, etc. In applying the chemical an effective amount and concentration of the toxicants of this invention is, of course, employed.

The terms "insecticide" and "insect" as used herein refer to their broad and commonly understood usage rather than to those creatures which in the strict biological sense are classified as insects. Thus, the term "insect" is used not only to include small invertebrate animals belonging to the class "Insecta", but also to other related classes of arthropods, whose members are segmented invertebrates having more or fewer than six legs, such as spiders, mites, ticks, centipedes, worms and the like.

What is claimed is:

1. A compound of the formula

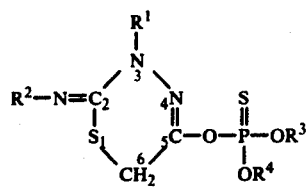

wherein $R^1$ is alkyl of 1 to 6 carbon atoms, $R^2$ is alkyl of 1 to 6 carbon atoms, alkenyl of 3 to 6 carbon atoms, cycloalkyl of 5 to 6 carbon atoms, phenyl or phenyl substituted with 1 to 2 substituents selected from the group consisting of alkyl of 1 to 4 carbon atoms, fluoro, chloro, bromo, iodo, nitro, trifluoromethyl, trichloromethyl, tribromomethyl, and alkoxy of 1 to 4 carbon atoms, $R^3$ is alkyl of 1 to 6 carbon atoms and $R^4$ is alkyl of 1 to 6 carbon atoms.

2. The compound of claim 1 wherein $R^1$ is alkyl of 1 to 6 carbon atoms, $R^2$ is alkyl of 1 to 6 carbon atoms, $R^3$ is alkyl of 2 to 4 carbon atoms and $R^4$ is alkyl of 2 to 4 carbon atoms.

3. The compound of claim 1 wherein $R^3$ and $R^4$ are ethyl.

4. The compound of claim 1 wherein $R^1$ is methyl, $R^2$ is t-butyl, and $R^3$ and $R^4$ are ethyl.

5. A method of killing insects which comprises contacting said insects or their habitats with an insecticidally effective amount of the compound defined in claim 1.

6. The method of claim 5 wherein $R^1$ is alkyl of 1 to 6 carbon atoms, $R^2$ is alkyl of 1 to 6 carbon atoms, $R^3$ is alkyl of 2 to 4 carbon atoms and $R^4$ is alkyl of 2 to 4 carbon atoms.

7. The method of claim 5 wherein $R^3$ and $R^4$ are ethyl.

8. The method of claim 5 wherein $R^1$ is methyl, $R^2$ is t-butyl, and $R^3$ and $R^4$ are ethyl.

9. An insecticidal composition which comprises a biologically inert carrier and an insecticidally effective amount of the compound defined in claim 1.

10. The composition of claim 9 wherein $R^1$ is alkyl of 1 to 6 carbon atoms, $R^2$ is alkyl of 1 to 6 carbon atoms, $R^3$ is alkyl of 2 to 4 carbon atoms and $R^4$ is alkyl of 2 to 4 carbon atoms.

11. The composition of claim 9 wherein $R^3$ and $R^4$ are ethyl.

12. The composition of claim 9 wherein $R^1$ is methyl, $R^2$ is t-butyl, and $R^3$ and $R^4$ are ethyl.

* * * * *